(12) United States Patent
Ten Kate (10) Patent No.: US 9,664,584 B2
(45) Date of Patent: May 30, 2017

(54) MONITORING THE CHANGE IN HEIGHT OF A DEVICE USING AN AIR PRESSURE SENSOR

(71) Applicant: KONINKLIJKE PHILIPS N.V., Eindhoven (NL)

(72) Inventor: Warner Rudolph Theophile Ten Kate, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 437 days.

(21) Appl. No.: 14/382,866

(22) PCT Filed: Mar. 11, 2013

(86) PCT No.: PCT/IB2013/051910
§ 371 (c)(1),
(2) Date: Sep. 4, 2014

(87) PCT Pub. No.: WO2013/136251
PCT Pub. Date: Sep. 19, 2013

(65) Prior Publication Data
US 2015/0025817 A1    Jan. 22, 2015

Related U.S. Application Data

(60) Provisional application No. 61/609,977, filed on Mar. 13, 2012.

(51) Int. Cl.
*G06F 19/00* (2011.01)
*G01L 27/00* (2006.01)
(Continued)

(52) U.S. Cl.
CPC .......... *G01L 27/002* (2013.01); *A61B 5/1117* (2013.01); *G01C 5/06* (2013.01);
(Continued)

(58) Field of Classification Search
CPC .. G08B 19/005; G08B 25/008; G08B 27/003; A43B 3/0005
(Continued)

(56) References Cited

U.S. PATENT DOCUMENTS 6,216,064 B1 * 4/2001 Johnson ................. G01C 5/005
244/76 R
6,266,623 B1 * 7/2001 Vock .................... A42B 3/0433
702/41

(Continued)

FOREIGN PATENT DOCUMENTS

CN        201829026 U     5/2011
DE    102008049750 A1     4/2010
(Continued)

OTHER PUBLICATIONS

Bianchi et al, "Barometric Pressure and Triaxial Accelerometry-Based Falls Event Detection", IEEE Transactions on Neural Systems and Rehabilitation Engineering, vol. 18, No. 6, Dec. 2010.

*Primary Examiner* — Edward Raymond (57) ABSTRACT

There is provided a method of monitoring a change in height of a device, the device comprising a sensor for measuring the air pressure at the device, the method comprising determining a pressure change threshold from a predetermined height change and an estimate or measurement of air pressure; obtaining a plurality of measurements of the air pressure at the device; determining a change in the air pressure from two or more of the measurements; and determining if the height of the device has changed by more than the predetermined height change using the determined change in the air pressure and the determined pressure change threshold.

15 Claims, 3 Drawing Sheets

(51) Int. Cl.
*A61B 5/11* (2006.01)
*G01C 5/06* (2006.01)
*G08B 21/04* (2006.01)
*G01L 7/00* (2006.01)

(52) U.S. Cl.
CPC .............. *G01L 7/00* (2013.01); *G08B 21/043* (2013.01); *G08B 21/0446* (2013.01); *A61B 5/1118* (2013.01); *A61B 2560/0242* (2013.01)

(58) Field of Classification Search
USPC .......................... 702/50, 150, 182–185, 188
See application file for complete search history.

(56) References Cited

U.S. PATENT DOCUMENTS

| | | |
|---|---|---|
| 2003/0136191 A1 | 7/2003 | Tsuji |
| 2010/0052896 A1 | 3/2010 | Goodman |
| 2011/0215925 A1 | 9/2011 | Chen et al. |
| 2011/0246114 A1* | 10/2011 | Jin .................... G08B 21/0446 702/94 |
| 2012/0016270 A1 | 1/2012 | Buhler et al. |

FOREIGN PATENT DOCUMENTS

| | | |
|---|---|---|
| EP | 1642248 A1 | 4/2006 |
| WO | 2004114245 A1 | 12/2004 |
| WO | 2010037564 A1 | 4/2010 |
| WO | 2010150117 A1 | 12/2010 |

\* cited by examiner

MONITORING THE CHANGE IN HEIGHT OF A DEVICE USING AN AIR PRESSURE SENSOR

CROSS-REFERENCE TO PRIOR APPLICATIONS

This application is the U.S. National Phase application under 35 U.S.C. §371 of International Application Serial No. PCT/IB2013/051910, filed on Mar. 11, 2013, which claims the benefit of U.S. Application Ser. No. 61/609,977, filed on Mar. 13, 2012. These applications are hereby incorporated by reference herein.

TECHNICAL FIELD OF THE INVENTION

The invention relates to a device that includes an air pressure sensor, and in particular relates to a method for monitoring the change in height of the device having improved accuracy and an apparatus that implements the method.

BACKGROUND OF THE INVENTION

Falling is a significant problem in the care of the elderly that can lead to morbidity and mortality. From a physical perspective, falls cause injuries, while from the mental perspective, falls cause fear-of-falling, which in turn leads to social isolation and depression.

Fall detection systems are available that can provide an automated and reliable means for detecting when a user has fallen. If a fall is detected, the system issues an alarm which summons help to the user. This assures the user that adequate measures will be taken in the event that a fall occurs.

Commonly, fall detectors are based on an accelerometer (usually a 3D accelerometer that measures acceleration in three dimensions) that is part of a device that is to be attached to the user's body. The signals from the accelerometer are processed to determine whether a fall has taken place. This processing can be performed in the device itself or in an associated base unit.

The reliability of fall detection can be improved by making use of further sensors which can be used to detect various different features that are characteristic of a fall. Important features include the impact of the user with the ground during the fall (which can also be detected by the accelerometer) and an orientation change as the user falls (which can be detected by the accelerometer and/or by a magnetometer and/or a gyroscope).

As a fall can be defined as "an event that results in a person coming to rest unintentionally on the ground or other lower level", another feature that can be detected is a change (primarily a reduction) in the height of the device above the ground. To this end, EP 1642248 proposes the use of an air pressure sensor to detect a change in the relative height measured by the device. Some currently available air pressure sensors make use of a membrane or diaphragm to measure the air pressure and are sensitive enough to be able to resolve changes in pressure equivalent to height changes of the order of 0.1 meter.

Typically, the air pressure P measured by a pressure sensor in a device is converted into altitude H according to $$H = H_0 + 44330\left(1 - \left(\frac{P}{P_0}\right)^{0.19}\right), \quad (1)$$

where $H_0$ and $P_0$ are the altitude and the air pressure at sea level respectively. Two subsequent measurements are compared to determine the change in height of the device.

However, this conversion formula is a complicated formula to implement in an electronic device. The conversion typically has to be executed for every measurement sample, which puts a significant load on the consumption of battery power. Although it is possible to simplify this equation by approximating it into a polynomial, every measurement sample has to pass the conversion routine. In addition, the polynomial expansion is an accurate approximation at sea level, but it deviates when the sensor is operated at higher altitudes (for example more than 1000 m above sea level).

It is important to correct for these and other inaccuracies in the processing since the height changes that a fall detection or other activity algorithm attempt to monitor are close to the detection accuracy of the air pressure sensor (i.e. often around 0.5 meters, which occur when the sensor is worn at the wrist or waist, where the user is relatively short and/or when monitoring for falls, or just the opposite, for rises from a bed or chair).

Therefore, there is a need for an improved way to process the measurements from an air pressure sensor to determine the change in height of a device that avoids the inaccuracies present in the prior art methods.

SUMMARY OF THE INVENTION

The invention provides that, rather than computing the altitude H according to equation (1) for each measurement sample from the air pressure sensor and comparing the computed altitudes to determine whether a predetermined change in height of the device has been exceeded, the detection threshold for the height change is changed instead to a corresponding pressure change threshold, and the difference between two air pressure measurements is evaluated using the pressure change threshold.

However, it is known that there is a different density of air at different altitudes which means that there is a different weight (pressure) increment with height decrement. This effect is accounted for in the conventional altitude conversion (equation (1)), but is not accounted for simply by assessing the height change in the pressure domain as described above. Therefore, to overcome this problem, the invention further provides that the pressure change threshold is periodically or intermittently adjusted based on the environmental air pressure at the device. In some embodiments, a default value for the pressure change threshold can be determined using, for example, the air pressure at sea level (typically 1013.25 hPa), or some other air pressure value that is preset based on the typical altitude at which the device is to be used. This default pressure change threshold can be used when the device is first activated and can be updated as actual air pressure measurements are collected by the device.

In particular, according to a first aspect of the invention, there is provided a method of monitoring a change in height of a device, the device comprising a sensor for measuring the air pressure at the device, the method comprising determining a pressure change threshold from a predetermined height change and an estimate or measurement of air pressure; obtaining a plurality of measurements of the air pressure at the device; determining a change in the air pressure from two or more of the measurements; and determining if the height of the device has changed by more than the predetermined height change using the determined change in the air pressure and the determined pressure change threshold.

Thus, this method avoids the need to convert every air pressure measurement to an altitude, as in the prior art, reducing the power consumption of the process. Instead, the pressure change threshold can be determined at an initial stage (for example during manufacture, testing or start up) from the required height change to be monitored and a default value for the environmental air pressure, or the pressure change threshold can be determined dynamically from the required height change to be monitored and the environmental air pressure, allowing the process to account for variations in the way pressure changes with altitude. As the altitude of the device is unlikely to change by a significant amount (i.e. of the order of 100 meters or more) in a short space of time, the pressure change threshold adaptation can be performed relatively infrequently (i.e. at a much lower rate than the air pressure sampling rate, and for example every minute, every 10 minutes, every 30 minutes, every hour, every 90 minutes, etc.). Furthermore, since a height difference value is to be converted to the pressure domain, instead of a value representing absolute height, more accuracy in the calculation is obtained.

A further issue with air pressure sensors, in particular those that make use of a membrane or diaphragm to measure the air pressure, is that their measurements are sensitive to accelerations experienced by the device, such as gravity, and are therefore sensitive to the orientation of the device.

In particular, gravity and other accelerations pull and push on the membrane of the pressure sensor and therefore the pressure measurement is dependent on the magnitude and direction of the acceleration acting on the device incorporating the pressure sensor. In particular, upon a change in orientation, which, as described above, commonly occurs during a fall, this pull/push effect may result in the measured height difference being quite different to the actual physical height that has been traversed between two air pressure measurements. Therefore, for accurate measurements, the computed altitude needs to be corrected or calibrated for the effect of accelerations on the membrane.

Techniques are available that determine a calibration factor during a calibration step that is performed during manufacturing or initial testing of the sensor. However, it has also been found that the calibration required is sensitive to the pressure in the environment around the sensor. In particular, when the environmental pressure is lower (such as at higher altitudes), the pull/push effect is relatively larger. It has been observed that where, say, a correction due to a change in direction of gravity to the altitude measurement of 0.2 meters is required when the sensor is at sea level, a correction due to a same direction change to the altitude measurement of 0.3 meters is required when the sensor is at an altitude of approximately 1600 meters.

Therefore, to overcome this problem, in some embodiments of the invention the air pressure measurements are corrected (calibrated) for the orientation of the device at the point the measurement was taken. Like the compensation for environmental air pressure, this calibration for sensitivity to accelerations, such as gravity, is done in the pressure domain, which makes the correction independent of altitude. In particular, the effective pressure that gravity or other accelerations superimpose on the air pressure measurement is determined, and this effective pressure is corrected for in each of the pressure measurements.

Therefore, in preferred embodiments of the invention, the method further comprises the steps of determining the effective pressure that gravity and/or other accelerations superimpose on each of the measurements of air pressure by the sensor and correcting each of the measurements of air pressure for the determined effective pressure.

Preferably, determining the effective pressure that gravity and/or other accelerations superimpose on a measurement of air pressure comprises obtaining a measurement of the acceleration acting on the device at or around the time that the measurement of air pressure at the device was made by the sensor and determining the effective pressure using the measurement of the acceleration and a calibration factor.

Preferably, the method further comprising the steps of obtaining a first measurement of the air pressure at the device and a first measurement of the acceleration experienced by the device while the device is in a first orientation and is not subject to any acceleration other than gravity, obtaining a second measurement of the air pressure at the device and a second measurement of the acceleration experienced by the device while the device is in a second orientation that is opposite to the first orientation and is not subject to any acceleration other than gravity and determining the calibration factor from the first and second measurements of air pressure and the first and second measurements of the acceleration.

Preferably, the step of determining the calibration factor comprises evaluating:

$$r = \frac{P_{up} - P_{down}}{a_{up} - a_{down}}$$

where $P_{up}$ and $P_{down}$ are the first and second measurements of air pressure respectively, and $a_{up}$ and $a_{down}$ are the first and second measurements of acceleration respectively, and r is the calibration factor.

Thus, by calibrating the measurements for the acceleration experienced by the sensor and by adapting the pressure change threshold for the environmental pressure, the calibration and observed pressure change are made independent of altitude.

Another issue with air pressure measurements is that air pressure is dependent on environmental temperature. A different temperature implies a different density of the air mass. At the same pressure but lower density (i.e. higher temperature) an altitude change will result in a smaller change of pressure, or, after conversion (using a conversion formula that uses a fixed temperature), a smaller change in height. This temperature dependence is of less severity to the orientation and acceleration calibration above, but it can become relevant when the detection of critical height differences is needed (such as in a fall detector application) and the sensor is to be used both outside and inside (since there can be significant temperature differences between the inside and outside of buildings).

While it is computationally complicated to account for temperature in the conversion to altitude, it has been found that it is fairly straightforward to do so in the computation of the pressure change threshold. Since it is necessary to know the environmental temperature, the sensing cannot be included in the same housing as the air pressure sensor, since it is close to the user's body and the temperature measurements will not be representative of the environmental temperature. Therefore, external information from either a separate temperature sensor or a database or other information source can be used in the determination of the pressure change threshold.

In preferred embodiments, the method described above further comprises the step of obtaining an estimate or a measurement of the temperature of the environment around the device and wherein the step of determining a pressure change threshold comprises determining the pressure change threshold from the threshold height change, at least one of the plurality of measurements of the air pressure at the device and the estimate or measurement of the temperature of the environment around the device.

In preferred embodiments, the step of determining a pressure change threshold comprises evaluating $\Delta P = -\gamma \Delta H$ where $\Delta P$ is the pressure change threshold, $\gamma$ is dependent on air pressure and temperature of the environment around the device and $\Delta H$ is the predetermined height change.

In particular embodiments, $\gamma$ is given by $$\gamma = 0.13 \frac{P^{0.81}}{T}$$

where P is the measurement of the air pressure at the device and T is the estimate or measurement of the temperature of the environment around the device. Alternatively, $\gamma$ is approximated using a linear dependence, $$\gamma \propto \frac{P}{T}.$$

Some further preferred embodiments of the method are set out below.

In some embodiments, the step of determining the pressure change threshold comprises determining the pressure change threshold from the predetermined height change and an estimate of air pressure at a predetermined altitude. This step can typically be performed during manufacturing, testing or an initial configuration procedure for the device.

In other embodiments, the step of determining the pressure change threshold comprises determining a pressure change threshold from the predetermined height change and at least one measurement of the air pressure at the device.

Preferably, the step of determining a pressure change threshold is repeated using at least one new measurement of the air pressure at the device.

In some embodiments, the step of determining a pressure change threshold is repeated after expiry of a predetermined time interval.

The step of determining a pressure change threshold preferably comprises evaluating $\Delta P \propto -\gamma \Delta H$ where $\Delta P$ is the pressure change threshold, $\gamma$ is dependent on pressure and $\Delta H$ is the predetermined height change.

Preferably, $\gamma$ is given by $\gamma = (4.42 \times 10^{-4})P^{0.81}$ where P is the measurement of the air pressure at the device. Alternatively, $\gamma$ is approximated using a linear dependence, $\gamma \propto P$.

In preferred embodiments, the method further comprises the step of averaging a plurality of the measurements to determine an average air pressure and wherein the step of determining a pressure change threshold uses the predetermined height change and the determined average air pressure.

In preferred embodiments, the step of determining if the height of the device has changed by more than the predetermined height change comprises comparing the determined change in the air pressure to the determined pressure change threshold.

In alternative embodiments, the step of determining if the height of the device has changed by more than the predetermined height change comprises normalizing the determined change in the air pressure and determining a likelihood that the height of the device has changed by more than the predetermined height change from the normalized change in air pressure.

According to a second aspect of the invention, there is provided an apparatus for monitoring a change in height of a device, the device comprising a sensor for measuring the air pressure at the device, the apparatus comprising a processing unit configured to determine a pressure change threshold from a predetermined height change and at least one of the plurality of measurements; receive a plurality of measurements of the air pressure at the device; determine a change in the air pressure from two or more of the measurements; and determine if the height of the device has changed by more than the predetermined height change using the determined change in the air pressure to and the determined pressure change threshold.

In further embodiments of the invention, the processor in the apparatus can be configured to perform any of the other method steps described above.

According to a third aspect of the invention, there is provided a user device that is configured to be worn by a user, the user device comprising an air pressure sensor that measures the air pressure at the user device; and an apparatus as described above.

According to a fourth aspect of the invention, there is provided a system, comprising a user device that is configured to be worn by a user, the user device comprising an air pressure sensor that measures the air pressure at the user device; and a base unit or other electronic device that is remote from the user device and that is configured to communicate with the user device to receive measurements of the air pressure at the device, the base unit or other electronic device comprising an apparatus as described above.

According to a fifth aspect of the invention, there is provided a computer program product, comprising a computer readable medium having computer program code embodied therein, the computer program code being configured such that, when executed by a suitable computer or processor, the computer or processor performs the method as described above.

BRIEF DESCRIPTION OF THE DRAWINGS

Embodiments of the invention will now be described, by way of example only, with reference to the following drawings, in which.

DETAILED DESCRIPTION OF THE PREFERRED EMBODIMENTS

Although the invention will be described below in terms of its use in a system for detecting falls by a user (in which a detected reduction in height of a user-worn device that is greater than a predetermined height change is indicative that a fall may have taken place), it will be appreciated that the invention can be used in other types of devices or systems, such as devices for monitoring the physical activity of users (for example that calculate the energy expended or power exerted during activity, or that monitor the type of activity such as walking, sitting, lying, and standing), devices for detecting and evaluating a sit-to-stand transfer (perhaps to provide an indication of fall risk) and devices for detecting whether a user is getting out of bed (particularly for post-surgery patients in a hospital environment). It will also be appreciated that the techniques described below are not limited to identifying a reduction in the height of the device, but are readily usable for identifying a corresponding increase in the height of the device (which might be useful for, say, determining if a user has got up after a suspected or detected fall and therefore causing a fall alarm to be revoked). Finally, it will be appreciated that the invention is applicable to any type of device or system that uses an air pressure sensor to monitor changes in height.

Figure 1:
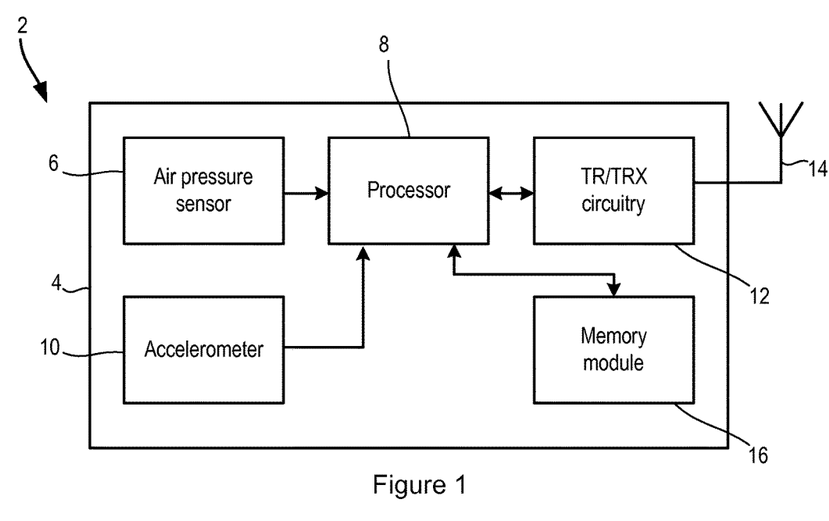
FIG. 1 is a block diagram of a device comprising an air pressure sensor according to an embodiment of the invention.

FIG. 1 illustrates an exemplary fall detection system 2 that implements a method of monitoring height changes in accordance with the invention. The fall detection system 2 comprises a user device 4 that is to be worn by a user. The user device 4 can be provided in the form of a pendant with a neck cord for placement around the user's neck, but alternatively the user device 4 can be configured to be worn at or on a different part of the user's body, such as the wrist, waist, trunk, pelvis or sternum, and will comprise a suitable arrangement for attaching the user device 4 to that part of the body (for example a belt or a strap).

The user device 4 is used to measure the air pressure at the user device 4 and to process those measurements to determine if the height of the user device has changed by more than a set amount. In this illustrated embodiment, the user device 4 is also used to measure the accelerations experienced by the user, and these measurements are processed to determine whether they exhibit various characteristics associated with a fall, such as a free-fall, impact (with the ground) and a motionless state following the impact.

Thus, the user device 4 of the fall detection system 2 comprises an air pressure sensor 6 that measures the air pressure at the device 4. The air pressure sensor 6 typically comprises a membrane or diaphragm that flexes or displaces as the air pressure changes, with the degree of flexing or displacement being used to generate an electrical signal indicative of the air pressure being measured. The air pressure sensor 6 can be a micro-electromechanical system (MEMS) air pressure sensor. The air pressure sensor typically produces measurement samples at a frequency of around 1.8 or 2 Hz, although it will be appreciated that many other sampling frequencies can be used (for example 50 or 100 Hz). The measurements of pressure can be expressed in any suitable metric.

The air pressure sensor 6 outputs its measurements to a processor 8 that processes the measurements according to the invention.

The user device 4 also comprises an accelerometer 10 that measures acceleration along three orthogonal axes. The signals output by the accelerometer 10 are provided to the processor 8 for analysis. The accelerometer 10 can be a micro-electromechanical system (MEMS) accelerometer. The acceleration experienced by the accelerometer 10 can be sampled at a rate of 30 Hz, although it will be appreciated that many other sampling frequencies can be used (for example 50 or 100 Hz).

In this embodiment, the user device 4 further comprises transmitter or transceiver circuitry 12 and associated antenna 14 that can be used for transmitting the results of the processing to a remote (base) unit or for placing an emergency call to a call centre (whether via the base unit or directly) to summon help in the event that a fall is detected. In either case, the transmitter or transceiver circuitry 12 can make use of any suitable wireless communication protocols, including, but not limited to, WiFi, Bluetooth, Zigbee, infra-red (IR), GSM, CDMA and LTE.

In this illustrated embodiment, the user device 4 also comprises a memory 16 that is used for storing measurements from the air pressure sensor 6 and/or accelerometer 10, and for storing the results of the processing by the processor 8.

Although not illustrated, the user device 4 may optionally comprise an audible alarm unit that can be triggered by the processor 8 if a fall is detected. This alarm can summon help to the user. Indeed, in low-end fall detection systems, the transmitter or transceiver circuitry 12 could be omitted, with the processor 8 summoning help to the user using the audible alarm unit.

A further optional component is a help button (not illustrated) that can be pressed by a user to summon help regardless of whether a fall has been detected.

In further embodiments, the fall detection system 2 (particularly the user device 4) may contain further sensors, such as a gyroscope, magnetometer and/or air flow sensor, whose signals can be processed to determine, or to assist in determining, height, orientation or other characteristics associated with a fall or user activity.

It will be appreciated that only components of the fall detection system 2 that are required for explaining the invention have been illustrated in FIG. 1, and a fall detection system 2 according to the invention may include further components and functionality to those described herein. For example, it will be appreciated that a user device 4 in a fall detection system 2 will include some form of power source or supply and circuitry for controlling the operation of the device 4.

Although in the illustrated embodiment of the invention the processing of the sensor measurements is performed by the processor 8 in the user device 4, it is possible in alternative embodiments for the main part of the processing of the sensor measurements to be performed remotely from the user device 4, which can have the effect of reducing the computational power consumption and/or computational complexity of the user device 4 (which may need to be traded against transmission power and complexity of the total system). In these alternative embodiments of a fall detection system 2, the processing of the air pressure sensor 6 and/or accelerometer 10 measurements can be performed in a base unit that is separate to the user device 4 worn by the user (not shown in FIG. 1). In that case, the air pressure sensor and/or accelerometer measurements can be transmitted or streamed (perhaps with some compression or pre-processing) from the user device 4 to the base unit via the transceiver circuitry 12 (allowing processor 8 and/or memory module 16 to be omitted). In a further alternative embodiment, the user device 4 may perform some of the initial processing steps on the air pressure sensor and/or accelerometer measurements before transmitting the results to a base unit which, for example, completes the processing and determines whether the height of the user device 4 has changed by more than a predetermined amount.

Before the invention is described in detail, some background information on the effect of altitude on barometric pressure measurements is provided below.

The air column above a device 4 has a weight, which, when expressed as force/area, translates into pressure. A decrease in altitude leads to an increase in the total weight, which can be sensed in terms of air pressure. The increase in weight is proportional to the decrease in height and proportional to the (local) mass density. For an ideal gas its pressure is proportional to its density (more particles per unit volume leads to an increase in pressure) and proportional to temperature (heating the volume causes the pressure to increase). In other words, the mass density is proportional to air pressure and inversely proportional to temperature. So, in first order, the weight increment, and hence the pressure increase dP, due to a small height decrement −dH is proportional to the current pressure, inversely proportional to temperature, and proportional to the height decrement:

$$dP \propto \rho \cdot -dH \propto (P/T) \cdot -dH \quad (2)$$

where $\rho$ is the air mass density, and P and T are pressure and temperature, respectively. Solving equation (2) yields an exponential dependence when assuming T is constant. However, since temperature decreases with higher altitude, a more sophisticated dependence results as shown in equation (1), but repeated here for ease of reference:

$$H = H_0 + 44330\left(1 - \left(\frac{P}{P_0}\right)^{0.19}\right) \quad (3)$$

where $H_0$ and $P_0$ are the altitude and the air pressure at sea level (typically 1013.25 hPa and 0 meters, respectively). A temperature of 288K at sea level is used.

As described above, there are some issues with using an air pressure sensor for height estimation.

Firstly, barometric pressure constantly fluctuates, which translates to variations in the estimated height.

Secondly at different altitudes there is a different density of air and hence a different weight (pressure) increment with height decrement. This effect is accounted for in the conversion formula equation (3), but is less accurately treated when using an approximation of the formula.

Thirdly, the acceleration experienced by the air pressure sensor affects the pressure measurement. The most significant and frequent cause of these errors results from acceleration due to gravity accompanied by a change in orientation of the sensor between measurements. This effect is also altitude dependent—i.e. accelerations have a larger effect at higher altitudes.

Fourthly, the air pressure is also dependent on the environmental temperature. As a consequence, the amount at which air pressures changes with a height change is also temperature dependent. Temperature gradient is accounted for in equation (3). However, in detecting changes, the dependence in equation (2) is needed. When the sensor is typically used inside a building, the temperature is within a small range and can be treated as a constant. However, when the sensor can also be used outside, there may be a larger range of differences between the inside and outside temperatures and therefore this effect is larger.

Further accuracy can be gained by taking this effect into account. It will be appreciated that this problem concerns the 'environmental temperature', i.e. the temperature of the air in the space around the user, not necessarily the temperature at the air pressure sensor. For example, when the sensor is being used outside during winter and the sensor is worn beneath the coat of the user, the air temperature at the sensor will be close to body temperature, but the 'environmental temperature' is likely to be much closer to 273K. It is the environmental temperature that should be taken into account when assessing any correction required to the air pressure measurement by the sensor.

Fifthly, the pressure measurement by the air pressure sensor is dependent on the temperature of the sensor itself. This, however, is already compensated for in the sensor reading software according to the specification of the sensor manufacturer.

Finally, the air pressure sensor can be used in a device that is for use in environments where the pressure is artificially higher than in the environment, such as in an airplane or in a shower (caused by the heat and restricted air flow). By assuming natural environmental pressure, a height estimation algorithm may determine inaccurate height changes. For example, if the user happens to fall in the shower, the sensed air pressure change may be of different magnitude than it would be in (e.g.) the living room. The algorithm may consider the sensed height difference (which by the assumptions in the conversion algorithm is way off) as an 'outlier', interpreting it as an indicator of a reduced likelihood of witnessing a fall event. So, the event is rejected and considered a false alarm.

Barometric fluctuations are fundamental. In detection theory it is tested whether the measured value surpasses a threshold. That threshold is chosen on the basis of the ratio between the probability that the measured value surpasses that threshold if the event is present and the probability that the measured value surpasses that threshold when the event is not present. Those probabilities depend on the magnitude of the value change (when the event is present and not present) and the variance in that value (and the chosen threshold). Larger value change and smaller variance improve detection quality. Vice versa, if the variance and the expected value change are known, then the likelihood of whether an observed value change is due to chance or due to an event being present can be estimated. Together with the likelihood of the other features (impact, orientation change) a decision on whether the event is present can be taken. So, at higher variance in air pressure, the algorithm can be configured for a larger height change before it is decided that a fall is being witnessed.

In accordance with embodiments of the invention, many of the above issues can be addressed by expressing height (and optionally acceleration) sensitivity in terms of pressure (force/area), by detecting pressure changes instead of height changes, and by regularly updating the pressure change detection threshold to the current environmental situation. The environmental pressure can easily be measured by the air pressure sensor. In further embodiments, the environmental temperature is measured by a temperature sensor that is located separately to the user device 4 (for example in a base unit in embodiments that include such a unit) or estimated from information in a database or another source using the known weather conditions, current season (i.e. spring, summer, autumn or winter) and/or information on whether the device 4 is inside or outside a building, and the temperature is also used to update the pressure change detection threshold.

Figure 2:
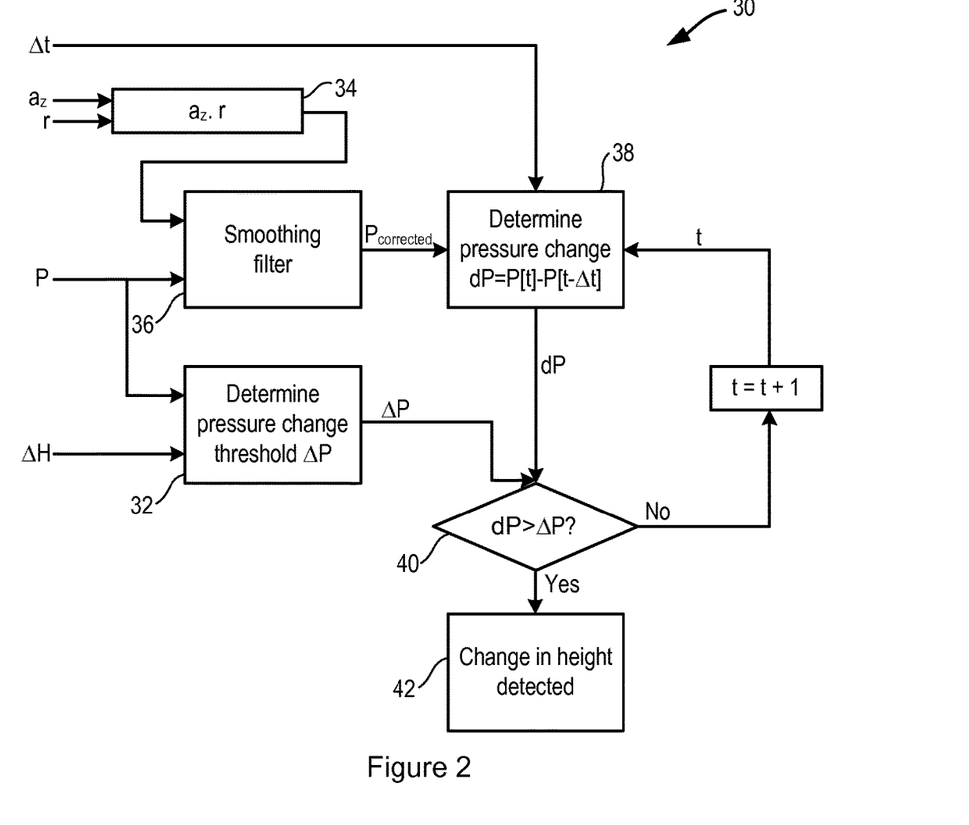
FIG. 2 is a block diagram of the processing algorithm executed to determine a change in height according to an embodiment of the invention.

A block diagram of an exemplary algorithm 30 for implementing an embodiment of the invention is illustrated in FIG. 2. This algorithm 30 can be implemented within processor 8, or within a processor in a base unit or computer that is remote from the user device 4. Although this algorithm 30 is described as being for use in detecting a fall (i.e. corresponding to a pressure rise), it will be appreciated that the algorithm 30 is easily adapted to additionally or alternatively detect an increase in height.

Firstly, the threshold height change ΔH that the algorithm 30 aims to detect is defined. This can be defined at the manufacturing or assembly stage of the user device 4, or can alternatively be adapted to the specific characteristics of the user (such as their height and where on their body they wear or carry the user device 4). A typical value for the threshold height change ΔH is 0.5 meters, but it will be appreciated that other values can be used, depending on the position on the body of the user that the device 4 is to be worn and/or the types of activity/movement to be monitored. A suitable range of values could be anything upwards of 0.1 meters, for example the range 0.1 meters to 1.2 meters. The value of the threshold height change ΔH can be stored in the memory module 16.

A time scale Δt over which this threshold height change is to be detected is also defined and can be stored in the memory module 16. A typical time scale Δt is 0.5-2 seconds, but it will be appreciated that other values can be used, for example up to 5, 8, 10 or 12 seconds, depending on the types of activity/movement to be monitored.

As described above, the threshold height change ΔH (in meters) is converted into a threshold pressure change ΔP. In particular, processing block 32 receives the threshold height change ΔH and one or more measurements of the pressure P from the air pressure sensor 6 and derives the threshold pressure change ΔP therefrom. This threshold can be computed at a low rate compared to the sampling rate of the air pressure sensor 6, for example every minute, every 10 minutes, every 30 minutes, every hour, every 90 minutes, etc. In this way, the processing required in the algorithm is reduced (and power consumption reduced), since it is not necessary to convert each air pressure measurement into a respective height. In some embodiments, the threshold height change to threshold pressure change conversion formula is derived as follows. Firstly, equation (3) is rewritten as $$P = P_0\left(1 - \frac{H - H_0}{44330}\right)^{5.255} \quad (4)$$

Then, the first order (series) approximation of equation (4) is taken from which H−H₀ is eliminated using equation (3) to arrive at $$\Delta P \propto -\gamma \Delta H \quad (5)$$

where $$\gamma = (1.19 \times 10^{-4}) P_0^{0.19} P^{0.81} = (4.42 \times 10^{-4}) P^{0.81} \quad (6)$$

P will be known from the recent measurements from the air pressure sensor 6, for example by averaging the measurements obtained over a time period $t_p$, say, the last minute:

$$P = \frac{1}{N} \sum_{k=0}^{N-1} P[k] \quad (7)$$

where P[k] is the air pressure measurement at instant k, and $N = f_s t_p$ the number of samples in the time period $t_p$ and $f_s$ is the sampling frequency of the air pressure sensor 6. It will be appreciated that in alternative embodiments other averages (i.e. estimation of the central point) of the measurements obtained over a time period $t_p$ can be taken, such as the mode or median.

It will also be appreciated that alternative approximations of equation (4) can be taken which will provide different representations of γ to that given in equation (6). For example, $\gamma = (1.19 \times 10^{-4}) P$ could be such an approximation.

Hence, the detection criterion in equations (5) and (6) account for environmental altitude. Compared to conventional algorithms, evaluation of equation (3) for each sample is replaced by a lower rate evaluation of equation (6), which, as described above, could be evaluated for example every minute, every 10 minutes, every 30 minutes, every hour, every 90 minutes, etc. Optionally, the evaluation of equation (6) can be simplified using approximation techniques, possibly using different approximations for different ranges of the measured P.

In some embodiments of the invention, an initial or default pressure change threshold value can be determined from the predetermined height change ΔH using a preset value for the air pressure at sea level (for example 1013.25 hPa) or any other altitude at which the device 4 is expected to be typically used. This initial pressure change threshold value could even be determined during the manufacture or testing of the device 4 and stored in the memory module 16. This default pressure change threshold can be used when the device 4 is first activated and can be updated as actual air pressure measurements are collected by the device 4.

As described above, gravity and other accelerations translate into a force on the membrane or diaphragm of the air pressure sensor 6. The force is proportional to the mass of the membrane or diaphragm and to the magnitude and direction of the gravity/acceleration. The component of gravity/acceleration that is perpendicular to the plane of the membrane or diaphragm divided by the (effective) area of the membrane or diaphragm induces an offset in the air pressure measurements.

By measuring the air pressure while the air pressure sensor 6 is not subject to any acceleration other than gravity with membrane in an 'up' orientation and with membrane in the opposite 'down' orientation, a calibration factor r between the air pressure offset and acceleration can be calibrated from $$r = \frac{P_{up} - P_{down}}{a_{up} - a_{down}} \quad (8)$$

where $P_{up}$ and $P_{down}$ are the pressure measurements (or averaged pressure measurements) when the air pressure sensor 6 is in the 'up' and 'down' orientations respectively, and $a_{up}$ and $a_{down}$ are the corresponding accelerations averaged over the same measurement period as measured by an accelerometer 10 that is in a fixed (i.e. non-moving) relationship with the air pressure sensor 6. The measurements provided by the accelerometer 10 in this procedure are 'calibrated' values, i.e. the acceleration measurements are passed through a calibration routine (typically a matrix multiplication) and those calibrated values used in setting the value of r in equation (8). Those skilled in the art will appreciate that it is possible to use a simplified calibration routine that does not involve a matrix multiplication, but instead applies an offset and gain correction per axis (since a matrix multiplication also accounts for crosstalk effects between the axes: e.g. acceleration along the x-axis affects the measurement for the y-axis). The offset sets the zero-acceleration point, the gain the scaling. Usually the gain is close to 1, but the offset cannot be neglected. If $a_{up}$ has a positive offset, $a_{dn}$ will have a negative offset, and using equation (8) without the calibration will provide an erroneous outcome.

If it is assumed that the stiffness of the membrane is constant, i.e. independent of environmental pressure, then the calibration factor r is independent of environmental altitude.

The calibration factor r can be determined during manufacture or testing of the user device 4 and stored in the memory module 16 of the device 4.

In algorithm 30, a processing block 34 computes the air pressure measurement correction by multiplying the (calibrated) acceleration in the direction perpendicular to the plane of the membrane ($a_z$ which has the same sign as $a_{up}$) measured by the accelerometer 10 by the calibration factor r and combines the correction with the measurements from the air pressure sensor 6 to give the corrected pressure sensor measurements $P_{corrected}$. In equation form, $$P_{corrected} = P - r \cdot a_z \quad (9)$$

In the illustrated algorithm 30, equation (9) is implemented with a smoothing filter block 36, but it will be appreciated that equation (9) can be implemented in a separate block to the smoothing filter.

As an alternative approach, the calibration factor r can be considered as a 3D vector, in which case it is not necessary to directly determine the component of acceleration that is perpendicular to the membrane, and the effective pressure applied by the acceleration/gravity can be given by the vector dot product of r and the acceleration vector.

The smoothing filter block 36 filters the obtained corrected pressure sensor measurements, $P_{corrected}$, using a smoothing filter, such as a low-pass filter, moving average (MA) filter, median filter, or a combination thereof, in order to remove or suppress noise in the air pressure measurements.

The corrected and smoothed air pressure measurements $P_{corrected}$ are provided to block 38 that determines the difference between two pressure sensor measurements that are $\Delta t$ apart. In particular, block 38 computes the change in pressure, dP, for each time instant t, as follows $$dP = P[t] - P[t - \Delta t] \quad (10)$$

The determined change in pressure dP is compared by block 40 with the threshold pressure change $\Delta P$ determined in block 32, and if the change in pressure dP exceeds the threshold pressure change $\Delta P$ a change in height of at least $\Delta H$ is detected (block 42). If the change in pressure dP does not exceed the threshold pressure change $\Delta P$, no change in height greater than $\Delta H$ is detected and the algorithm evaluates the next pair of corrected pressure sensor measurements in block 38.

Thus, it can be seen that the corrected air pressure measurements $P_{corrected}$ are independent of environmental altitude, while the threshold is adapted according to the altitude (through P in equation (6)). This means that, for example, at a higher altitude a lower threshold pressure change results. Consequently, while the gravity compensation $r \cdot a_z$ stays the same, it has a relatively larger effect.

As described above, in further embodiments of the invention, it is desirable for the height change evaluation to be independent of environmental temperature T. Environmental temperature T is needed, not the temperature of the air pressure sensor 6 (which is used internally to correct the sensor measurements), nor a temperature obtained close to the body of the user. Measuring environmental temperature poses additional requirements on the device/system design and hence has to be traded with the obtainable (and needed) gain in accuracy. The temperature difference that may occur between inside and outside, e.g. when freezing or during extreme seasonal heat periods, however, can be substantial enough to warrant a correction (also depending on the height change to be detected). The temperature may be measured by a sensor that is separate to the user device 4 (for example located in a base unit associated with the user device 4) or obtained from a database (such as a remote weather database or a database in the device 4, base unit or remote location that stores seasonal temperatures from which the user device 4 can select the appropriate value based on the current time and date and/or based on whether the device 4 is currently inside or outside a building).

The effect of temperature at a given pressure, e.g. induced by a given altitude, is to change the air density, i.e. the mass density. Therefore, the (local) effect of temperature on the change in pressure due to a height change is expressed by equation (2), and γ can be seen to be inversely proportional to T. So, we can modify equation (6) to $$\gamma = 1.19 \cdot 10^{-4} \frac{T_0}{T} P_0^{0.19} P^{0.81} = 0.034 \frac{P_0^{0.19} P^{0.81}}{T} = 0.13 \frac{P^{0.81}}{T} \quad (11)$$

where $T_0 = 288.15$ K, and T is the current (environmental) temperature (in K). As $T_0$ is the temperature at sea level, equation (11) is not fully accurate for higher altitudes. However, for practical usage, $T_0$ can be used. It will also be appreciated that approximations can be taken which will provide different representations of γ to that given in equation (11). For example, $$\gamma = 0.034 \frac{P}{T}$$

could be such an approximation.

As described above, in an airplane environment the pressure is artificially controlled and may deviate from the assumed 1000 hPa. The pressure increase due to a particular altitude decrease is given by the weight (increase) of the traversed air column. This weight is proportional to the air density, and hence to the local (environmental) pressure. Therefore, when using equations (5) and (6) to detect a height change, the height change is observed independently of effects due to the pressurized environment.

Also as described above, when the user is in a shower, the environmental pressure and environmental temperature effects should be accounted for. By doing so, height changes that happen in circumstances like a shower should be more easily and reliably detected.

Figure 3:
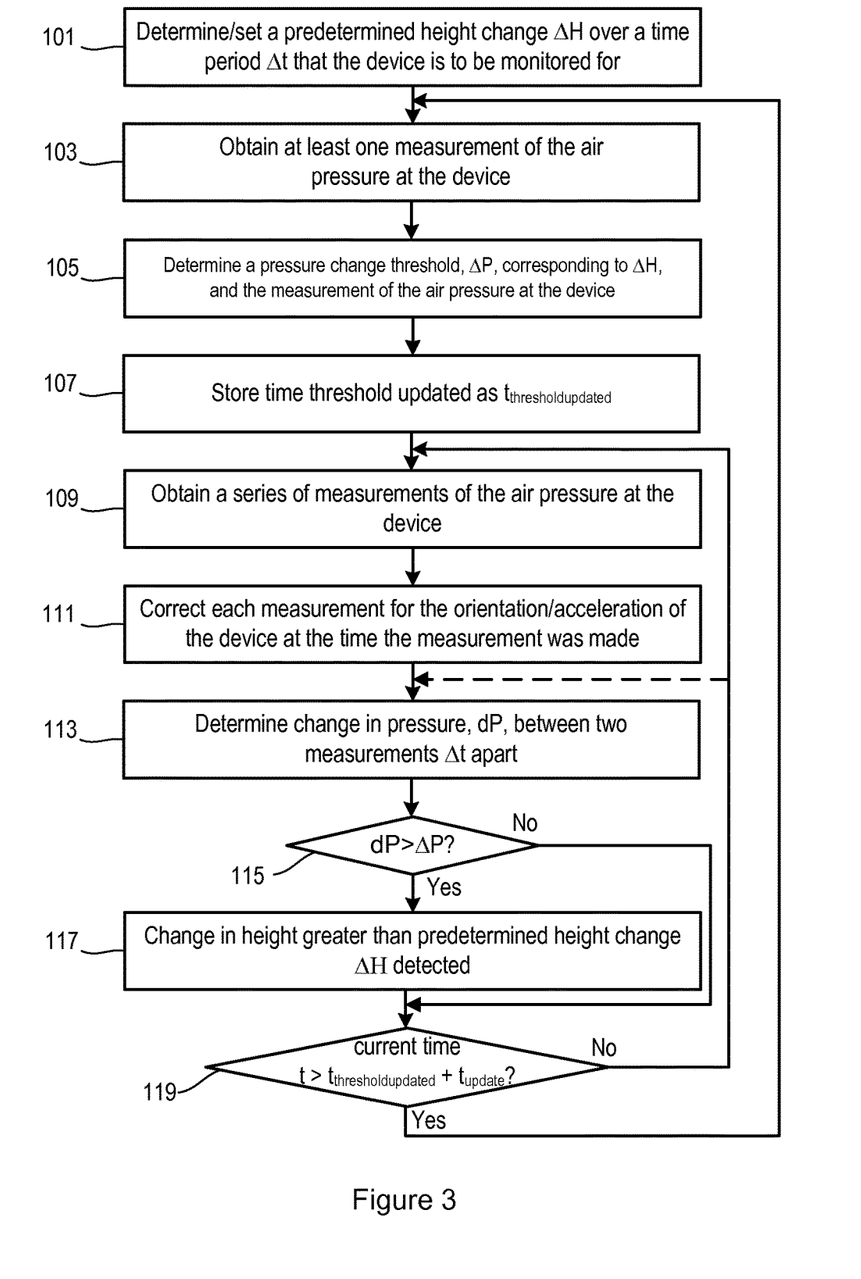
FIG. 3 is a flow chart illustrating a method of monitoring the height change of a device according to an embodiment of the invention.

FIG. 3 is a flow chart illustrating a method performed according to an embodiment of the invention. As the method generally corresponds to the algorithm shown in FIG. 2, the method will not be described in detail.

The method begins in step 101, in which the height change $\Delta H$ that is to be detected is determined or set, along with the time period $\Delta t$ over which that height change is to be observed. Step 101 is a step that is typically performed during a manufacturing or initial user setup phase.

Then, during use of the user device 4, at least one measurement of the air pressure at the device 4 is obtained using the air pressure sensor 6 (step 103).

Next, in step 105, a threshold pressure change $\Delta P$ is determined from the predetermined threshold height change ΔH and the at least one measurement of the air pressure obtained in step 103. The threshold ΔP is determined as set out in equations (5) and (6) above.

The time at which the pressure change threshold ΔP is determined/updated is stored as $t_{thresholdupdated}$ in the memory module 16 (step 107). It will be appreciated however that alternative implementations are conceivable, such as starting a count-down or count-up clock.

In step 109, a series of air pressure measurements are obtained by the air pressure sensor 6 in the device 4.

The measurements obtained in step 109 are each corrected for the orientation of/acceleration acting on the device 4 at the time each measurement was taken (step 111). This step makes use of measurements of the acceleration acting on the device 4 that were obtained during the same time period as the series of air pressure measurements. As described above, the correction to the air pressure measurements is determined by multiplying the measured component of acceleration that is perpendicular to the plane of the membrane or diaphragm in the air pressure sensor 6 by a calibration factor r that was determined during manufacture or testing of the device 4.

Once the air pressure measurements have been corrected in step 111, the change in pressure dP over the predetermined time period Δt is determined for two of the corrected air pressure sensor measurements.

In step 115, the determined change in pressure dP is compared to the updated pressure change threshold ΔP, and if the change in pressure dP exceeds the pressure change threshold ΔP, then a change in height greater than the predetermined height change ΔH is detected (step 117). In some cases, the device 4 can immediately issue an alarm or alert that the user of the device 4 may have fallen. In alternative implementations, the detection of a pressure change greater than ΔP can be used to trigger the computation or detection of other characteristics associated with a fall in other measurements of the activity or movement of the user. If one or more other characteristics are detected (the characteristics depending on the specific algorithm used to detect a fall), then the device 4 can issue an alarm or alert that the user of the device 4 may have fallen. Those skilled in the art will appreciate that many different algorithms can be used to detect a fall from a detected height change and one or more other detected characteristics (as well as appreciating that another characteristic of a fall can be detected first, and the detection of this characteristic used to trigger the evaluation of the height change using the air pressure sensor measurements).

If the change in pressure dP does not exceed the pressure change threshold ΔP, then a change in height less than the predetermined height change ΔH has been detected. Fall detection processing may continue on other measurements of the movement or activity of the user, although this depends on the fall detection algorithm used in the device 4.

After either of steps 115 and 117, the method passes to step 119 in which it is determined whether the pressure change threshold is to be updated again. In particular, it is determined whether the current time t exceeds the sum of the last threshold update time ($t_{thresholdupdated}$) and an update interval $t_{update}$ (which can be, for example, 1 minute, 10 minutes, 30 minutes, 1 hour, 90 minutes, etc.). Although not shown in FIG. 3, it will be appreciated that there may be other reasons to trigger an update to the pressure change threshold. For example, if the device 4 has not been used for some time (e.g. the measured acceleration exhibits a low variance), starting to use the device 4 again may trigger a pressure change threshold update procedure requiring a new air pressure measurement to be taken (assuming of course that a pressure change threshold update procedure is not performed while the user device 4 is not being used—i.e. measured acceleration exhibits low variance). As another example, detecting that the device 4 has moved from inside a building to outside, or vice versa, may trigger a pressure change threshold update procedure.

If it is not time to update the pressure change threshold ΔP (i.e. the current time is less than $t_{thresholdupdated}+t_{update}$), then the method returns to step 113 to evaluate a further pair of corrected air pressure measurements or to step 109 to obtain further measurements of air pressure for evaluation.

If it is time to update the pressure change threshold ΔP, the method returns to step 103 and a new measurement(s) of the air pressure is obtained and used to update (recalculate) the threshold pressure change ΔP. Although FIG. 3 shows sequential processing of updating the pressure change threshold and testing for the required pressure change, it will be appreciated that it is possible for the updating and testing processes to run independently and in parallel.

It will be appreciated that although the invention has been described as comparing the determined pressure change to a single pressure change threshold, it is possible for the algorithm to determine and update multiple pressure change thresholds corresponding to respective changes in height of the device 4. In this way, it is possible for the algorithm to provide an indication of the actual change in height traversed by the device (for example if a 0.5 meter height change threshold is exceeded but a 0.75 meter height change threshold is not exceeded, then it can be determined that the actual change in height of the device was between those two threshold values). As the threshold pressure change values are relatively straightforward to compute, monitoring for multiple height changes does not significantly increase the computational requirements of the device 4 over a single threshold solution.

It will also be appreciated that, rather than performing a direct comparison between the detected pressure change dP and the pressure change threshold ΔP, it is possible in some alternative embodiments of the invention to normalize the detected pressure change dP using the pressure change threshold ΔP or γ from equations (6) or (11) (the use of γ, or a proportional part of it, yielding likelihood in the height domain) and then to use the normalized pressure change to estimate a likelihood, or similar measure, for input into a fall detection classifier that assesses the likelihood of a fall having occurred from the likelihood of the height change exceeding the predetermined amount and optionally other features detected in the movements or activity of the user.

There is therefore provided an improved way of processing measurements from an air pressure sensor to determine the change in height of a device (and in particular whether the change in height is less or greater than a threshold height change) that avoids the inaccuracies and computational requirements of the prior art methods.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of

The invention claimed is:

1. A method of monitoring a change in height of a device, the device comprising a sensor for measuring the air pressure at the device, the method comprising:
   determining a pressure change threshold from a predetermined height change and an estimate of air pressure or a measurement of air pressure at the device;
   obtaining a plurality of measurements of the air pressure at the device;
   determining a change in the air pressure from two or more of the plurality of measurements; and
   determining if the height of the device has changed by more than the predetermined height change using the determined change in the air pressure and the determined pressure change threshold.

2. A method as claimed in claim 1, wherein the step of determining the pressure change threshold comprises determining the pressure change threshold from the predetermined height change and an estimate of air pressure at a predetermined altitude.

3. A method as claimed in claim 1, wherein the step of determining the pressure change threshold comprises determining a pressure change threshold from the predetermined height change and at least one measurement of the air pressure at the device.

4. A method as claimed in claim 1, wherein the step of determining a pressure change threshold is repeated using at least one new measurement of the air pressure at the device.

5. A method as claimed in claim 1, wherein the step of determining a pressure change threshold comprises evaluating $$\Delta P \propto -\gamma \Delta H$$

where $\Delta P$ is the pressure change threshold, $\gamma$ is dependent on pressure and $\Delta H$ is the predetermined height change.

6. A method as claimed in claim 1, wherein the step of determining if the height of the device has changed by more than the predetermined height change comprises comparing the determined change in the air pressure to the determined pressure change threshold.

7. A method as claimed in claim 1, wherein the step of determining if the height of the device has changed by more than the predetermined height change comprises normalizing the determined change in the air pressure and determining a likelihood that the height of the device has changed by more than the predetermined height change from the normalized change in air pressure.

8. A method as claimed in claim 1, further comprising the steps of:
   determining the effective pressure that gravity and/or other accelerations superimpose on each of the measurements of air pressure by the sensor; and
   correcting each of the measurements of air pressure for the determined effective pressure.

9. A method as claimed in claim 8, wherein determining the effective pressure that gravity and/or other accelerations superimpose on a measurement of air pressure comprises:
   obtaining a measurement of the acceleration acting on the device at or around the time that the measurement of air pressure at the device was made by the sensor; and
   determining the effective pressure using the measurement of the acceleration and a calibration factor.

10. A method as claimed in claim 1, the method further comprising the step of:
    obtaining an estimate or a measurement of the temperature of the environment around the device;
    and wherein the step of determining a pressure change threshold comprises determining the pressure change threshold from the threshold height change, at least one of the plurality of measurements of the air pressure at the device and the estimate or measurement of the temperature of the environment around the device.

11. A method as claimed in claim 10, wherein the step of determining a pressure change threshold comprises evaluating:

$$\Delta P = -\gamma \Delta H$$

where $\Delta P$ is the pressure change threshold, $\gamma$ is dependent on air pressure and temperature of the environment around the device and $\Delta H$ is the predetermined height change.

12. A computer program product, comprising a computer readable medium having computer program code embodied therein, the computer program code being configured such that, when executed by a suitable computer or processor, the computer or processor performs the method as claimed in claim 1.

13. An apparatus for monitoring a change in height of a device that comprises an air pressure sensor for measuring the air pressure at the device, the apparatus comprising:
    a processing unit configured to:
        determine a pressure change threshold from a predetermined height change and an estimate of air pressure or a measurement of air pressure at the device;
        receive a plurality of measurements of the air pressure at the device;
        determine a change in the air pressure from two or more of the plurality of measurements; and
        determine if the height of the device has changed by more than the predetermined height change using the determined change in the air pressure to and the determined pressure change threshold.

14. A device that is configured to be worn by a user, the device comprising:
    an air pressure sensor that measures the air pressure at the device; and
    an apparatus as claimed in claim 13.

15. A system, comprising:
    a device that is configured to be worn by a user, the device comprising an air pressure sensor that measures the air pressure at the device; and
    a base unit or other electronic device that is remote from the device and that is configured to communicate with the user device to receive measurements of the air pressure at the device, the base unit or other electronic device comprising an apparatus as claimed in claim 13.

* * * * *